United States Patent [19]

Fischer

[11] Plant 4,113

[45] Sept. 27, 1977

[54] AFRICAN VIOLET PLANT NAMED RACHEL

[75] Inventor: Arnold W. Fischer, Fallbrook, Calif.

[73] Assignee: Geo. J. Ball, Inc., West Chicago, Ill.

[21] Appl. No.: 730,662

[22] Filed: Oct. 7, 1976

[51] Int. Cl.[2] ..... A01H 5/00

[52] U.S. Cl. ..... Plt./69

[58] Field of Search ..... Plt./69

*Primary Examiner*—Robert E. Bagwill

*Attorney, Agent, or Firm*—Rummler and Snow

[57] ABSTRACT

A new variety of African violet plant for greenhouse culture and potted plant production distinguished by its unique soft blue flowers which are characterized by petals having a fine white marginal edging, the flowers being held well above the foliage on strong upright peduncles, and by a strong growth habit that performs well under considerably less than optimum conditions.

1 Drawing Figure

BACKGROUND OF THE NEW PLANT

This new variety of African violet plant was discovered by me in 1973 as a seedling of unknown parentage growing among random pollinated plants being cultivated by me at Hanover, Germany, in connection with my efforts to develop a unique flower coloring coupled with a strong and durable growth. Because of the unusual coloration of the blossoms of this plant it was reproduced by me at Hanover, Germany, by means of leaf cuttings and subsequently propagated through successive generations in the same manner, which demonstrated to me that I had a unique plant in which its distinctive features were firmly fixed and would hold true. Propagation of this new plant is now being carried on at West Chicago, Ill., and at Woodburn, Ore., U.S.A., by means of leaf cuttings and division of shoots.

DESCRIPTION OF THE DRAWINGS

My new variety of African violet is illustrated by the accompanying full color photographic drawing which shows a view of a potted plant of the new variety in full bloom and a series of the flowers in full face display to illustrate coloration variations that may occur from time to time, the color rendition being as nearly true as it is reasonably possible to obtain by conventional professional photographic procedures.

DESCRIPTION OF THE NEW PLANT

The following is a detailed description of this new African violet plant based upon observation of greenhouse pot plants at West Chicago, Ill., during the spring and summer of 1976, the color descriptions being according to the R.H.S. Colour Chart of The Royal Horticultural Society of London, England.

THE PLANT

Origin: Seedling.
Parentage: Unknown.
Classification:
*Botanic.*—*Saintpaulia ionantha.*
*Commercial.*—African violet.
Form: Compact potted plant.
Height: 1 to 2 inches from soil line to uppermost foliage, 3 to 3¾ inches from soil line to the top of the flowers.
Growth: Condensed and vigorous with strong horizontally spreading petioles and sturdy upright peduncles.
Foliage: Abundant in quantity with a variable number of leaves.

*Size of mature leaf.*—2 to 3 inches wide, 2 to 3½ inches long.
*Shape of mature leaf.*—Orbicular with a sagittate base, an acute to obtuse apex, and crenate margins.
*Texture.*—Velutinous.
*Venation.*—Pinnately veined with veins pronounced on the under side.
*Color.*—Upper side — Yellow Green 147A. Under side — Either Greyed Green 194D or Greyed Red 181D with pink main veins and petioles, depending upon culture.
*Petioles.*—2 to 4 inches, averaging 3½ inches, for the mature leaf.

THE BUD

Form: Globular, becoming urn-shaped as it opens.
Size: ¼ to ⅜ inch in diameter just before opening.
Opening rate: Slow — 2 to 4 weeks from visible bud to opened flower.
Color:
*When sepals first divide.*—White 155A.
*When petals begin to unfurl.*—Purple 79C-D.
Sepals: Hooded over bud for a short period.
*Form.*—Spear-shaped and upstanding.
*Size.*—1/32 to 1/16 inch wide and 3/16 inch long.
*Curlback.*—Slight but appressed to petals.
*Color.*—Outside — Greyed Purple 184B.
Calyx: Funnel-shaped and synsepalous.
*Splitting.*—Splits to star shape.
*Aspect.*—Smooth on inside. Hairy on outside.
Peduncle: Length — 1½ to 2 inches, average 1¾ inches.
*Strength.*—Very strong and erect.
*Aspect.*—Velutinous.
*Color.*—Greyed Red 182B.

THE FLOWER

Blooming habit: Recurrent and continuous the year around, producing more flowers in spring and fall than in other periods.
Size of flower: Medium to large.
*Diameter.*—1¼ to 1¾ inch, 1¼ inch average.
*Depth.*—⅜ to ½ inch.
Shape of flower: Cupped when bloom first opens becoming flattened when full open.
Borne: The inflorescence is a cyme.
Petalage: Petals are basally connate.
*Number.*—5 when single with petaloid anthers; 10 when fully double, also with petaloid anthers.

*Arrangement.*—Gamopetalous.

*Form.*—Rotate with petals having slightly wavy margins. Zygomorphic when single.

*Texture.*—Soft.

*Appearance.*—Glittery on upper side and satiny on lower side.

*Color.*—Upper side — Violet Blue 89D with a more or less distinct White 155D margin, depending upon culture, up to 1/16 inch wide. Reverse side — Mottled Violet 88C and D.

Petaloids: 1 to 4 petaloid anthers.

*Size.*—⅛ to ½ inch, average ¼ inch.

*Color.*—Violet Blue 89D and White 155D.

Peduncle: Length — 1¾ to 2½ inches, average 2 inches.

*Strength.*—Sturdy and upright.

*Color.*—Greyed Red 182C.

Discoloration after full bloom: White edging becomes less distinct.

Effect of weather: Hot weather decreases flower life and causes some fading. Plants thrive in 80 to 90% relative humidity.

Persistence: Flowers hang on and turn brown at senescence.

Lasting quality: 10 to 14 days for the fully opened flower.

REPRODUCTIVE ORGANS

Stamens:

*Anthers.*—Number — 2 when single, each with 2 anther cells; 4 when double, each with 2 anther cells. Length: 1/16 to ⅛ inch. Arrangement: Basifixed, connate at apex.

*Filaments.*—1/16 to ⅛ inch long. Color: White 155A with and without a purple blush.

*Pollen.*—Color — Yellow 7A.

Pistils: Number — one.

*Style.*—¼ to ⅜ inch long. Color: Green at base, white to purple apex.

*Stigma.*—Color — Violet 88B.

Ovaries: Superior and velutinous.

Fruit: Normally none seen except where special attempts have been made to pollinate the flower.

This new variety of African violet plant is particularly distinguished by its unique soft blue flowers which have a fine white margin and which are borne on strong upright peduncles well above the foliage. The plant has a strong and durable growth habit and performs very well under considerably less than optimum conditions. Both the flowers and the foliage of this plant, as well as the general plant habit, endure and in many cases benefit from less light than do most other varieties of African violet plants.

I claim:

1. A new and distinct variety of African violet plant substantially as herein shown and described, characterized by its soft blue flowers which are delicately margined with a narrow band of white, by its strong and durable growth habit which performs well under much less than optimum conditions, and by its abundant year around production of flowers which are held on strong stems well above the foliage.

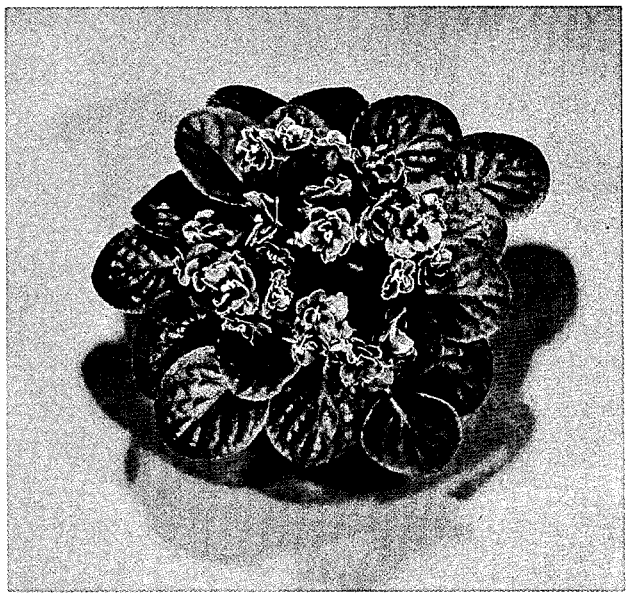
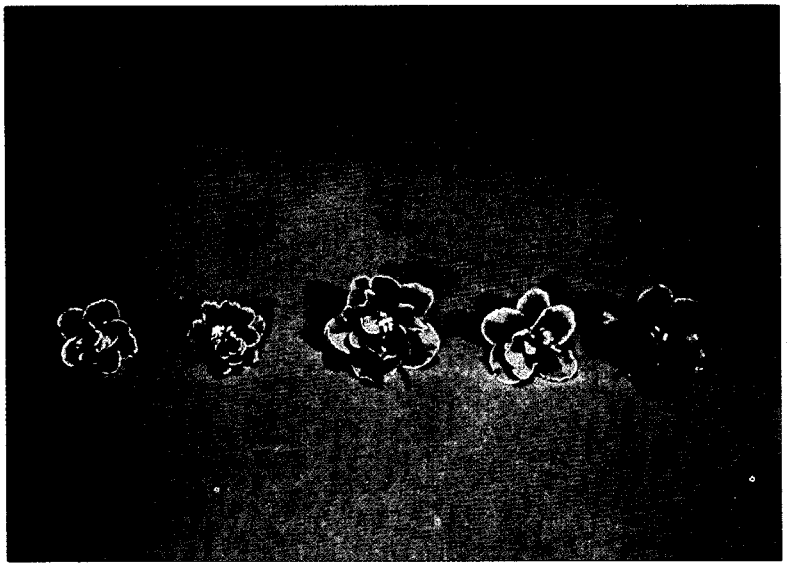

* * * * *